(12) United States Patent
Kim et al.

(10) Patent No.: US 8,283,477 B2
(45) Date of Patent: Oct. 9, 2012

(54) METHOD FOR PREPARING N-SUBSTITUTED MALEIMIDES

(75) Inventors: Jin-Eok Kim, Daejeon (KR); Seung-il Kim, Daejeon (KR); Han-Jin Kwag, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 12/999,420

(22) PCT Filed: Jun. 24, 2009

(86) PCT No.: PCT/KR2009/003405
§ 371 (c)(1),
(2), (4) Date: Dec. 16, 2010

(87) PCT Pub. No.: WO2010/018926
PCT Pub. Date: Feb. 18, 2010

(65) Prior Publication Data
US 2011/0124882 A1    May 26, 2011

(30) Foreign Application Priority Data
Aug. 11, 2008   (KR) .................. 10-2008-0078595

(51) Int. Cl.
*A61K 31/4015*  (2006.01)
*A61K 31/402*   (2006.01)
*C07D 207/40*   (2006.01)

(52) U.S. Cl. ........................... 548/451; 514/425

(58) Field of Classification Search .............. 548/451; 514/425
See application file for complete search history.

(56) References Cited

U.S. PATENT DOCUMENTS

| | | | |
|---|---|---|---|
| 2,444,536 A | 7/1948 | Searle | |
| 3,431,276 A | 3/1969 | Nield | |
| 4,623,734 A | 11/1986 | Kita et al. | |
| 4,780,546 A | 10/1988 | Kita et al. | |
| 4,786,738 A | 11/1988 | Kita et al. | |
| 4,851,547 A | 7/1989 | Kita et al. | |
| 4,980,483 A | 12/1990 | Kita et al. | |
| 5,973,166 A | 10/1999 | Mizori et al. | |

FOREIGN PATENT DOCUMENTS

| | | |
|---|---|---|
| EP | 0 257 831 A | 3/1988 |
| EP | 0 334 497 A | 9/1989 |
| EP | 0334497 A2 * | 9/1989 |
| JP | 52-13869 | 2/1977 |
| JP | 53-068770 | 6/1978 |
| JP | 57-042043 | 3/1982 |

OTHER PUBLICATIONS

Coleman, Lester E. et al.: "Reaction of Primary Aliphatic Amines with Maleic Anhydride", *Notes*, Jan. 1959, pp. 135-136.

* cited by examiner

*Primary Examiner* — Kamal Saeed
*Assistant Examiner* — Janet L Coppins
(74) *Attorney, Agent, or Firm* — Frommer Lawrence & Haug LLP; Ronald R Santucci

(57) ABSTRACT

The present invention relates to a method of preparing N-substituted maleimide in high purity and high yield, wherein, unlike a conventional method of preparing N-substituted maleimide after preparing N-substituted maleamic acid, an organic solvent, an acid catalyst, a dehydration co-catalyst and a stabilizer are added into a reactor without separately preparing N-substituted maleamic acid, and then a primary amine is added into the reactor to form an amine salt, maleic anhydride is added into the reactor, and the resulting mixture is subjected to a dehydration-cyclization reaction, wherein water produced during the reaction is azeotropically distilled with the organic solvent so as to effectively suppress formation of a maleimide polymer. Particularly, the invention simplifies the process, has high yield, minimizes side reactions, eliminates the introduction of expensive raw materials and the complicated treatment of the reaction solution and significantly shortens the time over which the raw materials and maleic anhydride are added.

20 Claims, No Drawings

METHOD FOR PREPARING N-SUBSTITUTED MALEIMIDES

This application is a 371 of PCT/KR2009/003405 filed on Jun. 24, 2009 published on Feb. 18, 2010 under publication number WO 2010/018926 A which claims priority benefits to Korean Patent Application Number 10-2008-0078595 filed Aug. 11, 2008, the disclosure of which is incorporated herein by reference.

TECHNICAL FIELD

The present invention relates to a method for preparing N-substituted maleimide.

BACKGROUND ART

N-substituted maleimides are useful as starting materials or intermediates for the preparation of pharmaceuticals, agricultural chemicals, dyes, polymer compounds and the like. Recently, they have been used in large amounts to improve the heat resistance of styrene resins and are also widely used in copolymers for resin modification or polymer compounding.

There have been known a few methods for preparing N-substituted maleimides. A conventional preparation method comprises allowing maleic anhydride to react with an amine to obtain N-substituted maleamic acid which is then subjected to dehydrocyclization (imidization). As one example, there is a method in which N-substituted maleamic acid obtained by heating maleic anhydride and amine at 180° C. is subjected to dehydrocyclization [L. E. Coleman et al., J. Org. Chem., 24, 135~136 (1959)]. However, this method is not economical, because the desired N-substituted maleimide is obtained in a yield of only about 15-50%.

Methods of preparing N-substituted maleimide in a relatively yield include methods in which a dehydrating agent or a dehydration catalyst is used for dehydrocyclization of N-substituted maleamic acid.

One example of the method that uses the dehydrating agent is disclosed in U.S. Pat. No. 2,444,536 in which N-substituted maleamic acid is dehydrocyclized using a dehydrating agent such as acetic anhydride in the presence of a sodium acetate catalyst. This method has a relatively high reaction yield, but it incurs a high production cost, because it uses a large amount of the dehydrating agent and carries out a complicated process of separating the product after the reaction. Thus, it is not an economical mass-production method.

Methods that are considered industrially advantageous include methods of dehydrocyclizing N-substituted maleamic acid under mild conditions using an effective dehydrating agent in place of the dehydrating agent. These methods do not use expensive sub-materials, and thus can be economically advantageous. U.S. Pat. No. 3,431,276 discloses a method of preparing N-substituted maleimides by heating and dehydrocyclizing N-substituted maleamic acid using an acid catalyst, such as sulfur trioxide, sulfuric acid or orthophosphoric acid, in a solvent having a suitable boiling point, without using a chemical dehydrating agent, and removing Thus produced water from the reaction system by azeotropic distillation. This method is advantageous in that an expensive dehydrating agent is not used and N-substituted maleimide can be easily separated, but the yield from the reaction is low and is likely to involve side reactions. In an attempt to improve this reaction yield, Japanese Patent Laid-Open Publication Nos. 53-68,770 and 57-42,043 disclose a method of preparing N-substituted maleimide by producing N-substituted maleamic acid, increasing the solubility of the N-substituted maleamic acid using an aprotic polar solvent such as dimethylformamide or dimethylsulfoxide and then dehydrocyclizing the N-substituted maleamic acid in the presence of an acid catalyst. The use of this aprotic polar solvent greatly increases the yield of N-substituted maleimide, but this solvent is expensive and highly toxic, and increases the production cost, because it is used in large amount. Also, this aprotic polar solvent can be deteriorated by the acid catalyst during the reaction, and thus needs to be used in a large amount. In addition, because this solvent has a high boiling point, much energy is required to separate the solvent from N-substituted male imide.

U.S. Pat. Nos. 4,623,734, 4,780,546 and 4,786,738 disclose methods comprising allowing maleic anhydride to react with amine in a non-polar organic solvent so as to produce N-substituted maleamic acid, and then dehydrocyclizing the N-substituted maleamic acid by azeotropic distillation in the presence of an acid stabilizer and other stabilizers. However, in the above methods, highly purified N-substituted maleimide cannot be prepared, and it is very difficult to separate the catalyst from the reaction solution after completion of the reaction due to the byproducts produced during the reaction. Even when the separation of the catalyst is achieved, the activity of the catalyst is rapidly reduced such that it cannot be effectively recycled. For the above reason, this method is not advantageous from an economical point of view.

U.S. Pat. No. 4,851,547 discloses supporting a catalyst on a solid carrier in order to facilitate the separation of the catalyst. This method appears to be suitable from an economical aspect, but reactors are required to be used separately, because maleic anhydride and amine are first allowed to react with each other to prepare N-substituted maleamic acid, and then an amine salt that was separately prepared is treated with acid and applied as a catalyst to the prepared N-substituted maleamic acid. Also, there is a problem that the N-substituted maleamic acid or the amine salt should be transferred in a slurry state. Furthermore, there is a problem in that a large amount of 2-amino-N-substituted succinimide is produced as a byproduct due to the use of an excessive amount of the amine during the reaction. In addition, because the amine that acts as a catalyst actually participates in the reaction, it is not suitable for the preparation of high-purity N-substituted maleimide.

U.S. Pat. No. 4,980,483 uses a two-stage reaction on the basis of the phenomenon in which the major byproduct 2-amino-N-substituted succinimide reacts with maleic anhydride so as to be selectively converted to N-substituted maleimide. According to the disclosure therein, in the former stage, a reaction is carried out using amine in an excess amount such that 2-amino-N-substituted succinimide can be produced, and in the latter stage, an excess amount of maleic anhydride is added, whereby N-substituted maleimide can be obtained in high yield and purity. However, a large amount of 2-amino-N-substituted succinimide is converted to N-substituted maleimide only under the condition that an excess amount of maleic anhydride is present, and non-converted 2-amino-N-substituted succinimide is an impurity present in the final product. For this reason, the above method is not suitable in a field requiring a high degree of purification. Also, 2-amino-N-substituted succinimide contained in the polymer compound can carbonize the surface of the polymer compound or make the surface of a final product irregular, and thus it should be removed.

U.S. Pat. No. 5,973,166 discloses a method in which a large amount of amine salt is used in place of an aprotic polar solvent to increase the solubility of reactants, intermediates and products in the prior-art maleimide preparation methods.

However, this method has problems occurring when N-substituted maleamic acid is prepared first, like other preparation methods. Also, it has a relatively low yield and has a problem in that the purification process using recrystallization is complex. In addition, it is not advantageous from an economical viewpoint, because the expensive amine salt is used in large amount.

DISCLOSURE

Technical Problem

Accordingly, the present inventors have studied on a preparation method for preparing N-substituted maleimide, which uses a simple reaction, has a high yield and minimizes side reactions, compared to conventional methods. As a result, the present inventors have developed a method of preparing N-substituted maleimide, wherein, unlike a conventional method of preparing N-substituted maleamic acid in advance, an acid catalyst, a dehydration co-catalyst and a stabilizer are added to an organic solvent, primary amine is added thereto to form an amine salt, and then maleic anhydride is added thereto, and the resulting mixture is subjected to a dehydration-cyclization reaction, whereby the introduction of expensive raw material and the complicated treatment of the reaction solution, which are the problems of the conventional method, are eliminated, an aprotic polar solvent of high-boiling point is not used, the purification process is simple, and the separation and recycling of the catalyst is easy. By developing this preparation method, the present invention has been completed.

Technical Solution

The present invention provides a method of preparing N-substituted maleimide in high purity and high yield, the method sequentially comprising: introducing an organic solvent, an acid catalyst, a dehydration co-catalyst and a stabilizer into a reactor; introducing a primary amine into the reactor to form an amine salt; introducing maleic anhydride into the reactor; and subjecting the resulting mixture to a dehydration-cyclization reaction, wherein water produced during the reaction is azeotropically distilled.

Advantageous Effects

It was found that the inventive method of preparing N-substituted maleimide using an amine salt as both a reactant and a catalyst could give a higher yield and result in higher purity than a conventional method of preparing N-substituted maleimide after preparing N-substituted maleamic acid. Also, it could be seen that the use of a suitable amount of tert-amine could result in a higher yield and purity. In addition, adding maleic anhydride in a suitable manner resulted in a higher yield.

BEST MODE

Hereinafter, the present invention will be described in further detail.

The present invention relates to a method of preparing N-substituted maleimide in high purity and high yield, wherein, unlike a conventional method of preparing N-substituted maleimide after preparing N-substituted maleamic acid, an organic solvent, an acid catalyst, a dehydration co-catalyst and a stabilizer are added into a reactor without separately preparing N-substituted maleamic acid, and then primary amine is added into the reactor to form an amine salt, maleic anhydride is added into the reactor, and the resulting mixture is subjected to a dehydration-cyclization reaction, wherein water produced during the reaction is azeotropically distilled with the organic solvent so as to effectively suppress formation of a maleimide polymer.

First, components that are used to prepare N-substituted maleimide according to the present invention will be described.

Examples of the primary amine that is particularly useful as a raw material for maleimide which is used in the present invention include methylamine, ethylamine, n-propylamine, i-propylamine, s-propylamine, n-butylamine, s-butylamine, i-butylamine, t-butylamine, n-hexylamine, n-dodecylamine, allylamine, benzylamine, cyclohexylamine, aniline, ethylaniline, toluidine, hydroxyaniline, nitroaniline and ethylenediamine.

The organic solvent that is used in the present invention must be insoluble in or immiscible with water, must be inactive in the reaction and must not participate in the reaction, such that water produced by the dehydrocyclization of N-substituted maleamic acid can be released from the reaction system by azeotropic distillation. Also, the boiling point thereof is preferably at least 50° C. for the reaction to proceed properly, but less than 170° C. for the stability of produced N-substituted maleimide. Examples of organic solvent suitable for use in the present invention include benzene, toluene, xylene, ethylbenzene, cumene, chlorobenzene, isopropylbenzene, mesitylene, t-butylbenzene, trimethyl hexane octane, and the like. So that the reaction proceeds properly and from an economical viewpoint, the amount of the organic solvent that is used in the reaction is preferably about 1-20 times the weight of primary amine used as a raw material, and more preferably about 2-10 times the weight of primary amine.

Also, the organic solvent should be selected in consideration of environmental factors, solubility for the raw material and the product, cost and handling easiness, and the selected solvent must be easily removed and suitably recycled after the reaction. Also, the organic solvents may be used alone or in combination, and the mixing ratio of the solvents can be determined so as to achieve the above object.

Preferred examples of an acid catalyst that may be used in the present invention include inorganic or organic monobasic or polybasic acids, such as anhydrous sulfuric acid, p-toluenesulfonic acid, orthophosphoric acid, metaphosphoric acid, pyrophosphoric acid, benzenesulfonic acid and trichloroacetic acid. This catalyst is used in an amount of about 10-200 molar parts, and preferably 20-100 molar parts, based on 100 molar parts of primary amine which is used in the reaction. If the catalyst is used in an amount of less than 10 molar parts, the reaction will not properly occur, and if it is more than 200 molar parts, it will reduce yield and result in side reactions.

Meanwhile, the catalyst may be supported on a carrier. Examples of a carrier that can support the catalyst include synthetic mineral materials, such as activated carbon, silica, silica-alumina, titanium dioxide and zirconium oxide, and natural mineral materials such as clay, talc, diatomaceous earth, bentonite and montmorillonite. Such an inorganic carrier is used in the form of powder or in the form of granules obtained by pelletizing and classifying the relevant substance. The catalysis is obtained with particularly desirable results when the carrier is made of such a porous substance as diatomaceous earth, silica gel or activated carbon. The amount of carrier applied is 0.2-4 times the weight of catalyst added, and preferably 0.5-2 times the weight of catalyst added.

When a catalyst binder is used together with the catalyst, it can increase the activity of the catalyst and makes it possible to recycle the catalyst. The catalyst binder must have low solubility in an organic solvent, must be physically or chemically bonded with the catalyst such that it is not separated from the catalyst, and must be easily mixed with reactants during the reaction. As the catalyst binder, polyalkylene glycol, polyvinyl alcohol or the like which have a molecule weight of 1000-10000 may be used. Preferably, polyethylene glycol (PEG) or polypropylene glycol (PPG) is used. The amount of catalyst binder used is 0.2-4 times the weight of catalyst added, and preferably 0.5-2 times the weight of the catalyst added.

The above reaction produces even better results when it is allowed to proceed in the presence of a metal-containing compound, as a dehydration co-catalyst, and a stabilizer. The metal-containing compound may be selected from the group consisting of oxides, acetates, maleates, succinates, and chlorides with at least one metal selected from the group consisting of zinc (Zn), chromium (Cr), palladium (Pd), cobalt (Co), nickel (Ni), iron (Fe) and aluminum (Al). Of these, zinc acetate proved to be particularly effective. The metal-containing compound is used in an amount of 0.005-5 molar parts, and preferably 0.01-4 molar parts, based on 100 molar parts of primary amine. If the dehydration co-catalyst is used in an amount of less than 0.005 molar parts, the reaction time will be increased, and if it is used in an amount of 5 molar parts, it will result in side reactions and reduce the activity of the catalyst.

Examples of the effective stabilizer in the present invention include methoxy benzoquinone, 2,6-t-butyl-4-methylphenol (BHT), p-methoxyphenol, phenothiazine, hydroquinone, alkylated diphenyl amines, methylene blue, tert-butyl catechol, tert-butyl hydroquinone, zinc dimethyldithiocarbamate, copper dibutyldithiocarbamate, alkylphenols, and alkylbisphenols. Concerning the amount of the stabilizer to be added, the addition of the stabilizer in a minute amount is not sufficiently effective and the addition thereof in an unduly large amount is undesirable because it affects the production of a final product, particularly a polymer compound. The stabilizer is used in an amount of 0.005-5 molar parts, and preferably 0.05-3 molar parts, based on 100 molar parts of primary amine. If the stabilizer is used in an amount of less than 0.005 molar parts, it can cause the formation of a maleimide polymer, and if it is used in an amount of more than 5 molar parts, it will excessively affect the final product such that it can act as a catalytic poison to the polymerization.

As described above, the present invention is characterized in that an amine salt is formed first by introducing an organic solvent, an acid catalyst, a dehydration co-catalyst and a stabilizer into a reactor and then introducing primary amine into the reactor. Particularly, when tert-amine acts as a co-catalyst before introducing the primary amine, the reaction conditions can be controlled to a mild condition. Namely, tert-amine may be used as a co-catalyst for a dehydration-cyclization reaction, and suitable tert-amine can control the acidity of the reaction system to control excessive reactions and can effectively suppress the production of a polymer from being formed by thus produced N-substituted maleimide. Examples of tert-amine that may be used in the present invention include trimethylamine, triethylamine, tripropylamine, tributylamine, tripentylamine, trioctylamine and tribenzylamine. The tert-amine is used in an amount of 0.05-50(0.01-50) molar parts, and preferably 0.01-20(0.05-20) molar parts, based on 100 molar parts of the primary amine. If the tert-amine is used in an amount of less than 0.05 (0.01) molar parts, it will not effectively suppress side reactions, and if it is used in an amount of more than 50 molar parts, it will reduce yield and make a washing process difficult.

In the present invention, maleic anhydride is added after the formation of the amine salt and is preferably used in an amount of 100-150 molar parts based on 100 molar parts of the primary amine. In addition to adding the maleic anhydride after formation of the amine salt as described above, additional maleic anhydride may also be added after the middle stage of the reaction in order to achieve a higher purity and yield. The amount of maleic anhydride that is additionally added is preferably 0.1-30 mole % based on the total amount of maleic anhydride used.

In the preparation method of the present invention, the reaction temperature is generally 50~200° C., and preferably 70~160° C. The pressure in the present invention is not specifically limited, but may be selected from reduced pressure, atmospheric pressure and elevated pressure. The reaction time varies depending on the type of solvent, the amount of raw material added and the reaction temperature, but is generally about 1-16 hours, and preferably 1-10 hours.

Following the reaction in the present invention can prepare N-substituted maleimide in high purity and high yield by introducing an organic solvent into a reactor, introducing an acid catalyst and, if necessary, a catalyst carrier, introducing a dehydration co-catalyst and a stabilizer, introducing tert-amine together with a primary amine for producing N-substituted maleimide so as to be partially or completely aminated, introducing maleic anhydride at one time or in portions, subjecting the resulting mixture to dehydration-cyclization, and removing thus produced water together with the organic solvent from the reaction system. The solvent and catalyst used in the reaction can be easily separated such that they may be used in another reaction without modification.

The present invention omits a separate process of making N-substituted maleamic acid, unlike conventional methods. Thus, only one reactor may be used, and a process of transferring N-substituted maleamic acid in a slurry state can be omitted, making the preparation process simple. Also, inconvenience associated with the transfer of N-substituted maleamic acid disappears, and the reaction can be completed in one reactor without needing to use a separate reactor. Moreover, it could be seen that the use of the method according to the present invention could provide a higher yield and purity than the method of preparing N-substituted maleimide after preparing N-substituted maleamic acid. More details will be described in the Examples below.

Unlike conventional methods in which the same kind of amine salt as an amine participating in the reaction is separately formed so as to be used as a catalyst, the present invention forms an amine salt from an amine participating in the reaction, thereby preventing an excessive amount of amine from being used in the reaction system. Thus, the major product 2-amino-N-substituted succinimide is not formed and is used in an equivalent amount, and thus the present invention is advantageous from an economical viewpoint. Also, in conventional methods, amine is added over a time ranging from 30 minutes to 1 hour or longer in order to avoid the formation of side reactions during the formation of N-substituted maleimide, whereas, in the present invention, an amine is added within 10 minutes, and thus the reaction time is shortened.

Unlike conventional methods in which maleic anhydride is added first into the organic solvent such that it is easily modified into maleic acid by water in the reaction system, the present invention can prevent maleic anhydride from being modified, because maleic anhydride is added into the prepared reaction system within a short time. Thus, the production of maleic acid from maleic anhydride or the production of fumaric acid from maleic anhydride by a rearrangement reaction can be prevented, thus providing a higher yield and purity than do the conventional methods.

MODE FOR INVENTION

Hereinafter, the present invention will be described in further detail with reference to examples, but the scope of the present invention is not limited thereto.

Example 1

Into a 300-ml reactor equipped with a thermometer, a cooler having a water separator attached thereto, and a stirrer, 88 g of a 1:1 mixed solvent of xylene and toluene was added. Then, 8 g (69.4 mmol) of 85% o-phosphoric acid was added and refluxed while stirring to remove water.

Then, 1.2 g (6.54 mmol) of zinc acetate and 1 g (4.54 mmol) of BHT were added. While stirring the reaction mixture, 20 g (214.8 mmol) of aniline was added for 5 minutes to form an amine salt, and 22 g (224.3 mol) of maleic anhydride was added into the reactor for 5 minutes. Then, the temperature of the reactor was increased to 125° C., and the content of the reactor was refluxed. Thus produced water was azeotropically distilled together with the mixed solvent to be removed from the reactor through the water separator. The reaction was performed at the temperature for 3 hours, and then 1.4 g of maleic anhydride was additionally added and allowed to react for 2 hours. The reaction was stopped, the content of the reactor was cooled to 30° C., and the catalyst layer was removed by layer separation. The xylene and toluene solution layers were transferred into a separate neutralization tank, and 50 g of 5% sodium carbonate aqueous solution was added thereto. The solution was stirred for 20 minutes and then allowed to stand for 20 minutes. The solution was separated clearly into an organic layer and an aqueous layer which was then separated and removed. 50 g of water was added to the organic layer, and the solution was stirred for 20 minutes and allowed to stand for 20 minutes. Thus formed aqueous layer was separated and removed. Thus separated organic layer was then transferred into a concentration tank, and then distilled under a reduced pressure of 20~130 mmHg at 50~100° C. to remove xylene and toluene. As a result, in the concentration tank, 27.0 g of a light-yellow solid material was obtained. The solid material was analyzed by liquid chromatography. The result showed 98% purity of N-phenylmaleimide, and 87% yield of N-phenylmaleimide based on aniline. As byproducts, 0.2% 2-amino-N-substituted succinimide and 1.2% N-phenylmaleimide dimer.

Example 2

Into a 100-L reactor equipped with a thermometer, a cooler having a water separator attached thereto, and a stirrer, 40 kg of xylene was added. Then, 2 kg of silica gel as a carrier was added, followed by 2 kg (17.3 mol) of o-phosphoric acid was added.

Then, 30 g (0.19 mol) of zinc acetate and 30 g (0.14 mol) of 2,4-dimethyl-6-t-butylphenol were added. 100 g (0.98 mol) of triethylamine was added to neutralize the solution, and then 4 kg (43.0 mol) of aniline was added into the reactor for 5 minutes to form an amine salt. Then, 4.6 kg (47.3 mol) of maleic anhydride was added into the reactor for 5 minutes. Then, keeping the temperature of the reactor at 140° C. while stirring, thus produced water was azeotropically distilled together with the xylene to be removed from the reactor through the water separator. The reaction was performed at the temperature for 6 hours. The reaction was stopped, the content of the reactor was cooled to 30° C., and the catalyst layer was removed by layer separation. The xylene solution layer was transferred into a separate neutralization tank, and 500 g of 5% sodium carbonate aqueous solution was added thereto. The solution was stirred for 20 minutes and then allowed to stand for 20 minutes. The solution was separated clearly into an organic layer and an aqueous layer which was then separated and removed. Then, 500 g of water was added to the organic layer, and the solution was stirred for 20 minutes and allowed to stand for 20 minutes. Thus formed aqueous layer was separated and removed. Thus separated organic layer was then transferred into a concentration tank, and distilled under a reduced pressure of 20~130 mmHg at 50~100° C. to remove xylene. After removal of the solvent, 7.2 kg of a light-yellow solid material was obtained in the concentration tank. The solid material was analyzed by liquid chromatography. The result showed 98% purity of N-phenylmaleimide, and 97% yield of N-phenylmaleimide based on aniline.

Example 3

Into a 100-L reactor equipped with a thermometer, a cooler having a water separator attached thereto, and a stirrer, 40 kg of xylene was added. Then, 2 kg of silica gel as a carrier was added, followed by 2 kg (17.3 mol) of o-phosphoric acid. Then, 30 g (0.19 mol) of zinc acetate and 30 g (0.14 mol) of 2,4-dimethyl-6-t-butylphenol were added. 200 g (1.98 mol) of triethylamine was added to neutralize the solution, and then 4 kg (43.0 mol) of aniline was added into the reactor for 5 minutes to form an amine salt. Then, 4.6 kg (47.3 mol) of maleic anhydride was added into the reactor for 5 minutes. Then, keeping the temperature of the reactor at 140° C. while stirring, thus produced water was azeotropically distilled together with the xylene to be removed from the reactor through the water separator. The reaction was performed at the temperature for 3 hours, and then 200 g of maleic anhydride was additionally added and allowed to react for 3 hours. Then, the reaction was stopped, the content of the reactor was cooled to 30° C., and the catalyst layer was removed by layer separation. The xylene solution layer was transferred into a separate neutralization tank, and 500 g of 5% sodium carbonate aqueous solution was added thereto. The solution was stirred for 20 minutes and then allowed to stand for 20 minutes. The solution was separated clearly into an organic layer and an aqueous layer which was then separated and removed. Then, 500 g of water was added to the organic layer, and the solution was stirred for 20 minutes and allowed to stand for 20 minutes. Thus formed aqueous layer was separated and removed. Thus separated organic layer was then transferred into a concentration tank, and distilled under a reduced pressure of 20~130 mmHg at 50~100° C. to remove xylene. After removal of the solvent, 7.3 kg of a light-yellow solid material was obtained in the concentration tank. The solid material was analyzed by liquid chromatography. The result showed the 99% purity of N-phenylmaleimide and 97% yield of N-phenylmaleimide based on aniline.

Example 4

Experiment was conducted in the same manner as Example 3, except that 300 g (2.94 mol) of triethylamine was added (addition time of primary amine: 5 min; addition time of maleic anhydride: 5 min). As a result, 7.3 kg of a light-yellow solid material was obtained in the concentration tank. The solid material was analyzed by liquid chromatography. The result showed 99% purity of N-phenylmaleimide and 98% yield of N-phenylmaleimide based on aniline.

Example 5

Experiment was conducted in the same manner as Example 2, except that 3 kg (26.0 mol) of o-phosphoric acid as a catalyst was added (addition time of primary amine: 5 min; addition time of maleic anhydride: 5 min). As a result, 7.1 kg of a brown-yellow solid material was obtained in the concentration tank. The solid material was analyzed by liquid chromatography. The result showed 97% purity of N-phenylmaleimide and 96% yield of N-phenylmaleimide based on aniline.

Example 6

Experiment was conducted in the same manner as Example 2, except that 1 kg (8.7 mol) of o-phosphoric acid as a catalyst was added (addition time of primary amine: 5 min; addition time of maleic anhydride: 5 min). As a result, 7.1 kg of a brown-yellow solid material was obtained in the concentration tank. The solid material was analyzed by liquid chromatography. The result showed 97% purity of N-phenylmaleimide and 96% yield of N-phenylmaleimide based on aniline.

Example 7

Experiment was conducted in the same manner as Example 2, except that 30 kg of xylene as a solvent was added (addition time of primary amine: 5 min; addition time of maleic anhydride: 5 min). As a result, 7.1 kg of a brown-yellow solid material was obtained in the concentration tank. The solid material was analyzed by liquid chromatography. The result showed 97% purity of N-phenylmaleimide and 96% yield of N-phenylmaleimide based on aniline.

Example 8

Experiment was conducted in the same manner as Example 3, except that 20 g (0.12 mol) of 6-butylcatechole as a stabilizer was added in place of 2,4-dimethyl-6-t-butylphenol (addition time of primary amine: 5 min; addition time of maleic anhydride: 5 min). As a result, 7.2 kg of a brown-yellow solid material was obtained in the concentration tank. The solid material was analyzed by liquid chromatography. The result showed 97% purity of N-phenylmaleimide and 97% yield of N-phenylmaleimide based on aniline.

Example 9

Experiment was conducted in the same manner as Example 3, except that 400 g of maleic anhydride was additionally added after 3 hours of the reaction (addition time of primary amine: 5 min; addition time of maleic anhydride: 5 min). As a result, 7.1 kg of a brown-yellow solid material was obtained in the concentration tank. The solid material was analyzed by liquid chromatography. The result showed 99% purity of N-phenylmaleimide and 98% yield of N-phenylmaleimide based on aniline.

Example 10

Experiment was conducted in the same manner as Example 3, except that 800 g of maleic anhydride was additionally added after 3 hours of the reaction (addition time of primary amine: 5 min; addition time of maleic anhydride: 5 min). As a result, 7.1 kg of a brown-yellow solid material was obtained in the concentration tank. The solid material was analyzed by liquid chromatography. The result showed 97% purity of N-phenylmaleimide and 97% yield of N-phenylmaleimide based on aniline.

Example 11

Into a 100-L reactor equipped with a thermometer, a cooler having a water separator attached thereto, and a stirrer, 40 kg of xylene was added. Then, 2 kg of silica gel as a carrier was added, after which 2 kg (17.3 mol) of o-phosphoric acid was added. Then, 30 g (0.19 mol) of zinc acetate and 30 g (0.14 mol) of 2,4-dimethyl-6-t-butylphenol were added. 200 g (1.96 mol) of triethylamine was added to neutralize the solution, and then 4 kg (43.0 mol) of cyclohexylamine was added into the reactor for 5 minutes to form an amine salt.

Then, 4.4 kg of maleic anhydride was added into the reactor for 5 minutes. Then, while keeping the temperature of the reactor at 140° C., thus produced water was azeotropically distilled together with the xylene to be removed from the reactor through the water separator. The reaction was performed at the temperature for 3 hours, and then 200 g of maleic anhydride was additionally added and allowed to react for 3 hours. Then, the reaction was stopped, the content of the reactor was cooled to 30° C., and the catalyst layer was removed by layer separation. The xylene solution layer was transferred into a separate neutralization tank, and 500 g of 5% sodium carbonate aqueous solution was added thereto. The solution was stirred for 20 minutes and then allowed to stand for 20 minutes. The solution was separated clearly into an organic layer and an aqueous layer which was then separated and removed. Then, 500 g of water was added to the remaining material, and the solution was stirred for 20 minutes and allowed to stand for 20 minutes. Thus formed aqueous layer was separated and removed. Thus separated organic layer was then transferred into a concentration tank, and distilled under a reduced pressure of 20~130 mmHg at 50~100° C. to remove xylene. After removal of the solvent, 7.1 kg of a light-white solid material was obtained in the concentration tank. The solid material was analyzed by liquid chromatography. The result showed 98% purity of N-cyclohexylmaleimide and 97% yield of N-cyclohexylmaleimide based on aniline.

Examples 12 to 17

Experiments were conducted under the conditions shown in Table 1 below in the same manner as Example 2. The results of Examples 12 to 17 are shown in Table 1.

TABLE 1

| | Acid catalyst | Solvent | Stabilizer | Addition time (min) | | purity (wt %) | Yield (based on aniline) |
| --- | --- | --- | --- | --- | --- | --- | --- |
| | | | | Primary amine | Maleic anhydride | | |
| Example 12 | o-phosphoric acid | Toluene | 2,4-dimethyl-6-t-butylphenol | 5 | 5 | 97 | 94 |

TABLE 1-continued

|  | Acid catalyst | Solvent | Stabilizer | Addition time (min) | | purity (wt %) | Yield (based on aniline) |
| --- | --- | --- | --- | --- | --- | --- | --- |
|  |  |  |  | Primary amine | Maleic anhydride |  |  |
| Example 13 | o-phosphoric acid | Toluene | t-butylcatechol | 5 | 5 | 98 | 94 |
| Example 14 | o-phosphoric acid | Ethylbenzene | 2,4-dimethyl-6-t-butylphenol | 5 | 5 | 97 | 95 |
| Example 15 | o-phosphoric acid | Ethylbenzene | t-butylcatechol | 5 | 5 | 98 | 95 |
| Example 16 | o-phosphoric acid | toluene/xylene(50/50v/v %) | 2,4-dimethyl-6-t-butylphenol | 5 | 5 | 97 | 97 |
| Example 17 | Sulfuric acid | Xylene | 2,4-dimethyl-6-t-butylphenol | 5 | 5 | 95 | 95 |

Example 18

Into a 300-ml reactor equipped with a thermometer, a cooler having a water separator attached thereto, and a stirrer, 88 g of a 1:1 mixed solvent of xylene and toluene was added. Then, 6.4 g of PEG-4000 as a catalyst binder was added, and 8 g (69.4 mmol) of 85% o-phosphoric acid was added and refluxed while stirring to remove water therefrom.

Then, 1.2 g (6.54 mmol) of zinc acetate and 1 g (4.54 mmol) of BHT were added. While the reaction solution was stirred, 20 g (214.8 mmol) of aniline was added for 5 minutes to form an amine salt, and 22 g (224.3 mol) of maleic anhydride was added into the reactor for 5 minutes. Then, the temperature of the reactor was increased to 125° C., and the content of the reactor was refluxed. Thus produced water was azeotropically distilled together with the mixed solvent, so that it was removed from the reactor through the water separator. The reaction was performed at the temperature for 3 hours, and then 1.4 g of maleic anhydride was additionally added and allowed to react for 2 hours. The reaction was stopped, the content of the reactor was cooled to 30° C., and the catalyst layer was removed by layer separation. The xylene and toluene solution layers were transferred into a separate neutralization tank, and 50 g of 5% sodium carbonate aqueous solution was added thereto. The solution was stirred for 20 minutes and then allowed to stand for 20 minutes. The solution was separated clearly into an organic layer and an aqueous layer which were then separated and removed. 50 g of water was added to the organic layer, and the solution was stirred for 20 minutes and allowed to stand for 20 minutes. Thus formed aqueous layer was separated and removed. Thus separated organic layer was transferred into a concentration tank, and distilled under a reduced pressure of 20~130 mmHg at 50~100° C. to remove xylene and toluene. After completion of the solvent, 33.2 g of a light-yellow solid material was obtained in the concentration tank. The solid material was analyzed by liquid chromatography. The result showed 99% purity of N-phenylmaleimide and 90% yield of N-phenylmaleimide based on aniline. As a byproduct, 1% 2-amino-N-substituted succinimide was observed.

Example 19

The catalyst separated from Example 18 above was used. 1 g of BHT was added into the reactor, and then 88 g of a 1:1 mixed solvent of xylene and toluene was added. The temperature of the reactor was increased to 100° C., and the content of the reactor was stirred. Then, the PEG layer was melted and mixed with the solvent. Here, 20 g of aniline was added for 5 minutes to form an amine salt. The reaction temperature was lowered to 50° C., and 22 g of maleic anhydride was added for 5 minutes. Then, the temperature of the reactor was increased to 125° C., and the content of the reactor was refluxed. Thus produced water was azeotropically distilled together with the mixed solvent, so that it was removed from the reactor through the water separator. The reaction was performed at the temperature for 3 hours, and then 1.4 g of maleic anhydride was additionally added and allowed to react for 2 hours. The reaction was stopped, the content of the reactor was cooled to 30° C., and the catalyst layer was removed by layer separation. The xylene and toluene solution layers were transferred into a separate neutralization tank, and 50 g of 5%, sodium carbonate aqueous solution was added thereto. The solution was stirred for 20 minutes and then allowed to stand for 20 minutes. The solution was separated clearly into an organic layer and an aqueous layer which was then separated and removed. 50 g of water was added to the organic layer, and the solution was stirred for 20 minutes and allowed to stand for 20 minutes. Thus formed aqueous layer was separated and removed. Thus separated organic layer was transferred into a concentration tank, and distilled under a reduced pressure of 20~130 mmHg at 50~100° C. to remove xylene and toluene. After completion of the solvent, 34.6 g of a light-yellow solid material was obtained in the concentration tank. The solid material was analyzed by liquid chromatography. The result showed 99% purity of N-phenylmaleimide and 94% yield of N-phenylmaleimide based on aniline. As a byproduct, 3% 2-amino-N-substituted succinimide was observed.

Example 20

This Example was conducted in the same manner as Example 18, except that PPG-2000 was used in place of PEG-4000 as the catalyst binder. As a result, 32.1 g of a light-yellow solid material was obtained in the concentration tank. The solid material was analyzed by liquid chromatography. The result showed 98% purity of N-phenylmaleimide and 88% yield of N-phenylmaleimide based on aniline. As byproducts, 1.2% 2-amino-N-substituted succinimide was observed, and a small amount of unknown byproducts were additionally observed.

Example 21

Experiment was conducted in the same manner as Example 19, except that the catalyst separated from Example 20 was used. As a result, 33.7 g of a yellow solid material was obtained in the concentration tank. The solid material was analyzed by liquid chromatography. The result showed 98% purity of N-phenylmaleimide and 93% yield of N-phenylmaleimide based on aniline. As byproducts, 1.2% 2-amino-N-substituted succinimide was observed, and a small amount of unknown byproducts were additionally observed.

Comparative Example 1

Into a 100-L reactor equipped with a thermometer, a cooler having a water separator attached thereto, and a stirrer, 20 kg of xylene was added. Then, 2 kg of silica gel as a carrier was added, after which 2 kg (17.3 mol) of o-phosphoric acid was added. Then, 30 g (0.19 mol) of zinc acetate and 30 g (0.14 mol) of 2,4-dimethyl-6-t-butylphenol were added. Into a separate 100-L reactor, 20 kg of xylene was added and then 4.6 kg (47.3 mol) of maleic anhydride was added for 5 minutes, and then the temperature of the reactor was adjusted to 80° C. and 4 kg (43.0 mol) of aniline was added dropwise to the reactor over 30 minutes. Thus produced N-phenylmaleamic acid was transferred into the reactor in which the catalyst had been put. Then, while keeping the temperature of the reactor at 140° C., thus produced water was azeotropically distilled together with the xylene to be removed from the reactor through the water separator. The reaction was performed at the temperature for 6 hours, and then the reaction was stopped, the content of the reactor was cooled to 30° C., and the catalyst layer was removed by layer separation. The xylene solution layer was transferred into a separate neutralization tank, and 500 g of 5% sodium carbonate aqueous solution was added thereto. The solution was stirred for 20 minutes and then allowed to stand for 20 minutes. The solution was separated clearly into an organic layer and an aqueous layer which was then separated and removed. Then, 500 g of water was added to the remaining material, and the solution was stirred for 20 minutes and allowed to stand for 20 minutes. Thus formed aqueous layer was separated and removed. Then thus separated organic layer was transferred into a concentration tank, and distilled under a reduced pressure of 20~130 mmHg at 50~100° C. to remove xylene. After removal of the solvent, 7.0 kg of a light-yellow solid material was obtained in the concentration tank. The solid material was analyzed by liquid chromatography. The result showed 96% purity of N-phenylmaleimide and 93% yield of N-phenylmaleimide based on aniline.

The invention claimed is:

1. A method of preparing N-substituted maleimide in high purity and high yield, the method comprising:
   introducing an organic solvent; an acid catalyst; polyalkylene glycol having a molecular weight of 1.000-10.000 as a catalyst binder; a dehydration co-catalyst selected from the group consisting of oxides, acetates, maleates, succinates, and chlorides with at least one metal selected from the group consisting a zinc (Zn), chromium (Cr), palladium (Pd), cobalt (Co), nickel (Ni), iron (Fe), and aluminum (Al); and a stabilizer into a reactor;
   introducing a primary amine into the reactor to form an amine salt;
   introducing maleic anhydride into the reactor; and
   subjecting the resulting mixture to a dehydration-cyclization reaction, wherein water produced during the reaction is azeotropically distilled.

2. The method of claim 1;
wherein the organic solvent is used in an amount equal to 1-20 times the weight of the primary amine.

3. The method of claim 2;
wherein the organic solvent is one or more selected from the group consisting of benzene, toluene, xylene, ethylbenzene, cumene, chlorobenzene, isopropylbenzene, mesitylene, t-butylbenzene, trimethyl hexane, and octane.

4. The method of claim 1;
wherein the acid catalyst is one or more selected from the group consisting of anhydrous sulfonic acid, p-toluene sulfonic acid, orthophosphoric acid, metaphosphoric acid, pyrophosphoric acid, benzenesulfonic acid and trichloroacetic acid.

5. The method of claim 1;
wherein the acid catalyst is used in an amount of 10-200 molar parts based on 100 molar parts of the primary amine.

6. The method of claim 1;
wherein the acid catalyst is added in a state supported on a carrier.

7. The method of claim 6;
wherein the carrier is used in an amount equal to 0.2-2 times the weight of the acid catalyst.

8. The method of claim 6;
wherein the carrier is one or more selected from the group consisting of activated carbon, silica, silica-alumina, titanium dioxide and zirconium oxide, natural mineral materials, clay, talc, diatomaceous earth, bentonite and montmorillonite.

9. The method of claim 1;
wherein the polyalkylene glycol is polyethylene glycol or polypropylene glycol.

10. The method of claim 1;
wherein the catalyst binder is used in an amount equal to 0.2-2 times the weight of the acid catalyst.

11. The method of claim 1;
wherein the dehydration co-catalyst is used in an amount of 0.005-5 molar parts based on 100 molar parts of the primary amine.

12. The method of claim 1
wherein the stabilizer is at least one selected from the group consisting of methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, alkylphenols, and alkylbisphenols.

13. The method of claim 1;
wherein the stabilizer is used in an amount of 0.005-5 molar parts based on 100 molar parts of the primary amine.

14. The method of claim 1;
wherein the primary amine is at least one selected from the group consisting of methylamine, ethylamine, n-propylamine, i-propylaminc, s-propylamine, n-butylamine, s-butylamine, i-butylamine, t-butylamine, n-hexylamine, n-dodecylamine, allylamine, benzylamine, cyclohexylamine, aniline, ethylaniline, toluidine, hydroxyaniline, nitroaniline and ethylenediamine.

15. The method of claim 1;
wherein tert-amine is additionally added before the primary amine is added.

16. The method of claim 15;
wherein the tert-amine is added in an amount of 0.05-50 molar parts based on 100 parts of the primary amine.

17. The method of claim 15;
wherein the tert-amine is at least one selected from the group consisting of trimethylamine, triethylamine, tripropylamine, tributylamine, tripentylamine, trioctylamine and tribenzylamine.

18. The method of claim 1;
wherein the maleic anhydride is added in an amount of 100-150 molar parts based on 100 molar parts of the primary amine.

19. The method of claim 1;
wherein the maleic anhydride is additionally added as required during the reaction.

20. The method of claim 1;
wherein the reaction is carried out at a temperature or 50-200° C.

* * * * *